(12) United States Patent
Kline et al.

(10) Patent No.: US 11,911,211 B2
(45) Date of Patent: Feb. 27, 2024

(54) YOKE FOR SENSING CAROTID STENOSIS

(71) Applicant: CVR Medical Corporation, Denver, NC (US)

(72) Inventors: Bret Kline, Columbus, OH (US); Peter Bakema, Denver, NC (US)

(73) Assignee: CVR Medical Corporation, Denver, NC (US)

( * ) Notice: Subject to any disclaimer, the term of this patent is extended or adjusted under 35 U.S.C. 154(b) by 656 days.

(21) Appl. No.: 15/737,165

(22) PCT Filed: Jun. 15, 2016

(86) PCT No.: PCT/US2016/037665
§ 371 (c)(1),
(2) Date: Dec. 15, 2017

(87) PCT Pub. No.: WO2016/205395
PCT Pub. Date: Dec. 22, 2016

(65) Prior Publication Data
US 2018/0168545 A1     Jun. 21, 2018

Related U.S. Application Data

(60) Provisional application No. 62/175,913, filed on Jun. 15, 2015.

(51) Int. Cl.
*A61B 8/00* (2006.01)
*A61B 5/02* (2006.01)
(Continued)

(52) U.S. Cl.
CPC .............. *A61B 8/4227* (2013.01); *A61B 7/00* (2013.01); *A61B 8/0891* (2013.01); *A61B 8/58* (2013.01);
(Continued)

(58) Field of Classification Search
CPC ....... A61B 5/6835; A61B 5/6822; A61B 7/00; A61H 2203/0425; A61H 2203/04; A61H 2205/04; A61F 5/00; A61F 5/024
See application file for complete search history.

(56) References Cited

U.S. PATENT DOCUMENTS 3,724,452 A * 4/1973 Nitschke ................. A61F 5/055
602/18
3,945,376 A * 3/1976 Kuehnegger ........... A61F 5/024
602/19
(Continued)

FOREIGN PATENT DOCUMENTS

JP     2000-060810 A     2/2000
JP     2008-241363 A     10/2008
(Continued)

OTHER PUBLICATIONS

International Search Report dated Sep. 29, 2016 of International Application No. PCT/US2016/037665.

*Primary Examiner* — Kaylee R Wilson
*Assistant Examiner* — Severo Antonio P Lopez
(74) *Attorney, Agent, or Firm* — Vos-IP, LLC

(57) ABSTRACT

A yoke for use with infrasonic sensing elements, where the yoke is Y shaped, flexible, and assists in positioning, on a human subject, the sensing elements appropriately on the carotid arteries and on the heart.

9 Claims, 13 Drawing Sheets

(51) Int. Cl.
*A61B 7/00* (2006.01)
*A61B 8/08* (2006.01)

(52) U.S. Cl.
CPC ... *A61B 5/02007* (2013.01); *A61B 2560/0214* (2013.01)

(56) References Cited

U.S. PATENT DOCUMENTS

| | | | | |
|---|---|---|---|---|
| 5,437,614 A | * | 8/1995 | Grim | A61F 5/022 602/19 |
| 5,727,558 A | * | 3/1998 | Hakki | A61B 5/6822 600/485 |
| 5,853,005 A | * | 12/1998 | Scanlon | A61B 5/113 600/459 |
| 5,876,361 A | * | 3/1999 | Harris | A61F 5/024 602/19 |
| 6,129,693 A | * | 10/2000 | Peterson | A61F 5/024 297/338 |
| 6,503,213 B2 | * | 1/2003 | Bonutti | A61F 5/055 602/5 |
| 6,662,032 B1 | * | 12/2003 | Gavish | A61B 5/486 600/323 |
| 2002/0143260 A1 | * | 10/2002 | Ogura | A61B 5/022 600/500 |
| 2003/0069506 A1 | * | 4/2003 | Chassaing | A61B 7/00 600/481 |
| 2003/0135127 A1 | * | 7/2003 | Sackner | A61B 5/6805 600/536 |
| 2003/0220594 A1 | * | 11/2003 | Halvorson | A61F 5/024 602/19 |
| 2005/0119573 A1 | * | 6/2005 | Vilenkin | A61B 5/02007 600/450 |
| 2005/0234349 A1 | | 10/2005 | Pravica et al. | |
| 2007/0043300 A1 | * | 2/2007 | Koblanski | A61B 5/1126 600/527 |
| 2007/0049848 A1 | * | 3/2007 | Koblanski | A61B 5/024 600/587 |
| 2007/0276270 A1 | * | 11/2007 | Tran | A61B 5/002 600/508 |
| 2008/0039733 A1 | * | 2/2008 | Unver | A61B 7/00 600/528 |
| 2008/0154140 A1 | * | 6/2008 | Chang | A61B 5/6822 600/500 |
| 2011/0004136 A1 | * | 1/2011 | Giontella | A61F 5/024 602/18 |
| 2011/0105971 A1 | * | 5/2011 | Ingimundarson | A61F 5/028 602/19 |
| 2012/0232427 A1 | * | 9/2012 | Bakema | A61B 7/04 600/586 |
| 2013/0116958 A1 | | 5/2013 | Kristensson et al. | |
| 2014/0194740 A1 | * | 7/2014 | Stein | A61B 8/0808 600/455 |
| 2014/0288473 A1 | * | 9/2014 | Matsushita | A61H 15/00 601/137 |
| 2014/0330187 A1 | * | 11/2014 | Perez | A61F 5/024 602/19 |
| 2015/0202072 A1 | * | 7/2015 | Glazener | A61F 5/05883 602/18 |
| 2015/0223962 A1 | * | 8/2015 | Yasui | A61F 5/024 602/19 |
| 2015/0272503 A1 | * | 10/2015 | Molden | A61B 5/0082 600/386 |
| 2015/0320323 A1 | * | 11/2015 | Bakema | B06B 1/06 600/586 |
| 2016/0121737 A1 | * | 5/2016 | Henningson | B60L 53/00 320/109 |
| 2016/0205568 A1 | * | 7/2016 | Loverich | H04W 52/0245 370/252 |

FOREIGN PATENT DOCUMENTS

| | | |
|---|---|---|
| JP | 2013-039375 A | 2/2013 |
| JP | 2013-172968 A | 9/2013 |
| JP | 2013-226008 A | 10/2013 |
| WO | WO/1997/007733 A1 | 3/1997 |
| WO | 2008120154 A2 | 9/2008 |
| WO | WO/2009/039863 A1 | 4/2009 |
| WO | WO/2011/163509 A1 | 12/2011 |
| WO | WO/2015/065988 A9 | 4/2016 |

* cited by examiner

YOKE FOR SENSING CAROTID STENOSIS

CROSS REFERENCE TO RELATED APPLICATIONS

This application is a National Phase Stage of International Application No. PCT/US16/37665, filed Jun. 15, 2016, which claims the benefit of U.S. Provisional Application Ser. No. 62/175,913, filed Jun. 15, 2015, which are hereby incorporated by reference in their entirety.

FIELD OF INVENTION

The present application is generally related to a yoke that is utilized in conjunction with sensing pods suitable for placing a respective sensing pod on each side of the neck, adjacent to the carotid artery and placing a third sensing pod adjacent to the heart, wherein the yoke provides support and structure to enable measurements to be taken by the sensing pods for determining stenosis of the carotid artery.

BACKGROUND OF THE INVENTION

Infrasonic acoustic signals generated by a living organism can be useful in the detection and diagnosis of certain conditions or ailments of the organism. In particular, blood flow in the organism cause infrasonic acoustic signals (e.g., via vibration of the arterial or venal walls) that indicate possible extent or stenosis, occlusion, or aneurysm in the organisms' arteries and/or veins.

Detection of stenosis in the carotid artery remains a challenge in the medical industry, yet remains a critical tool in evaluation of patients for possible heart attack, stroke, and other injuries related to blockage of the venous system. U.S. Pat. No. 7,621,875 describes one process for detecting arterial disease using, sensed infrasonic acoustic signals. As described therein, sensed infrasonic signals are analyzed by a computer or other similar device to generate a complex frequency grid of frequencies and associated lifetimes. A predictive model of complex frequencies associated with peak-perturbation acoustic signals attributed to boundary perturbations in vivo that occur with early stage arterial disease is provided. A predictive model of complex frequencies associated with line-perturbation acoustic signals attributed to boundary perturbations in vivo that occur with later stage arterial disease is also provided. It is then determined whether peak and/or line perturbation acoustic signals of the predictive models are present to detect whether the subject has arterial disease.

U.S. Pat. No. 5,853,005 discloses known transducers and acoustic pads for sensing acoustic signals in an organism. The devices shown in U.S. Pat. No. 5,853,005 are difficult to utilize, and can generate signal noise and/or spikes, which can be disruptive in proper analysis.

Quickly and easily setting up equipment to sense any acoustic signals at the proper locations on a subject can be of vital importance in an emergency. Even in nonemergency situations, ease of use is important in that it enables a medical technician (or possibly a patient) to administer the procedure and utilize the equipment without a doctor having to be present.

SUMMARY OF THE INVENTION

The present invention provides an improved yoke or array to be used in conjunction with sensing components for detecting infrasonic acoustic signals and for detecting stenosis in the carotid arteries.

In accordance with these and other objects, a first aspect of an invention disclosed herein is directed to an apparatus that provides for a wishbone or "Y" shaped array, having two arms and a stem with a longitudinal axis and a lateral axis. Arranged at one end of the stem is a "c" shaped shoulder extending from the stem along the lateral axis and connected to each end of the "c" shaped shoulder are the arms of the "Y". The arms and the distal end of the stem, each define a track section, which is suited for attaching a sensor pod thereto. The sensor pods attached to the track sections can be slideably moved along the track section to vary a position of the pod along a respective track section. Adjusting each sensor pod extends or shortens a distance between the sensor pods to accommodate users of different sizes. Accordingly, by use of the slideable sensors on each of the branches of the array, it is easy to extend or reduce the distance of an attached sensor on the arms or stem from the neck vertex.

A particular feature of the array is that the stem and the arms have a structure that provides a flexible but secure structure for movement and arrangement of the sensors on a body. The array is preferably a plastic material, having a bending modulus sufficient to be modified from its original form, but to return to its original form after use.

One aspect of the invention is an array for determining carotid artery stenosis in a human patient comprising: a curved stem section having a longitudinal axis and a lateral axis, a stem vertex, a neck vertex, a shoulder, and two arms. The curved stem section comprises a stem and a neck portion connected at a stem vertex such that the neck is positioned upwards at an angle of about 165° with respect to the stem. The neck connects to one side of the neck vertex and the shoulder is positioned to extend on each side of the neck vertex, generally along the lateral axis from the neck vertex, and two arms are connected to each side of the shoulder such that the angle between the neck and the shoulder/arms is about 90°. Each of the stem, neck, shoulder, and arms are made of a flexible plastic material that is capable of being flexed away from its resting state. The flexed material imparts a force to return back to its resting state.

One aspect of the invention is an array for use in a carotid artery sensor comprising a Y-shaped structure formed by a stem, a neck, a stem vertex, a neck vertex, shoulders, a left arm, and a right arm. The stem and neck are connected at the stem vertex such that the neck is biased upwards at an angle of about 165° with respect to the stem. The neck connects to the neck vertex on one side and the shoulders are connected to an adjacent side, with the left and right arms attached to each side of the shoulders, the shoulders and arms extend to the side of the vertex and are thus substantially perpendicular to the neck and extend to create a bell-like shape. The arms, are further positioned at an angle of about 90° away from the neck.

According to a preferred aspect of the invention, the arms extend from the shoulder and extend downward to form a bell shaped structure. The stem and the arms are preferably a plastic material, having a bending modulus sufficient to be modified from its resting form, but to return to its resting form after use. Alternatively, a suitable metal material may be used. The arms and stem have a semi-circular structure that provides a flexible but secure structure for movement and arrangement of the sensors on a body. Each of the stem and arms of the array functions as an extension track, and therefore allows attached sensors to the engage with the track and to slide along the track for proper positioning.

According to an embodiment, an array for determining carotid artery stenosis in a human patient is provided, comprising: a stem; a neck coupled to the stem and defining an angle of between 125° and 175°; a neck vertex coupled to the neck opposite the stem; and a pair of arms extending from the neck vertex, the pair of arms defining an angle of between 90° and 145°. Each of the legs and arms are made of a flexible plastic material that is configured to be flexed away from its resting state; and the flexible plastic material imparts a force to return back to its resting state.

In another embodiment, an array for use in a carotid artery sensor configured as a Y-shaped structure is provided having a neck; a stem; a stem vertex arranged between the neck and the stem; a neck vertex coupled to the neck opposite the stem vertex; and a left and a right arm coupled to the neck vertex. The neck and stem are connected via the stem vertex such that the neck is biased upwards at an angle of about 165 degrees, the left and right arms extend substantially perpendicularly from to the neck from the neck vertex, and the left and right arms create a bell-like shape.

In another embodiment an apparatus provides a Y-shaped array, comprising: two arms and a shoulder; a single angled leg having a longitudinal axis and a lateral axis; the single angled leg having a stem portion parallel to the longitudinal axis and a straight neck portion attached at a point such that the neck portion is positioned towards the vertical at a slight angle, the neck portion connected to the neck vertex and attached to the neck vertex is a shoulder, to which are attached the two arms, extending to opposite sides of the neck vertex and extending downward to form a bell shaped structure; and a respective sensor pod arranged on each of the two arms and the stem portion. The leg and the arms are a plastic material, having a bending modulus sufficient to be modified from its resting form, but to return to its resting form after use. The arms and legs have a semi-circular structure that provides a flexible but secure structure for movement and arrangement of the sensors on a body. Each of the legs and arms of the array functions as an extension track, and the attached sensors engage a respective extension track to selectively slide along the track for adjustable positioning.

Additional features and embodiments will be apparent to one of ordinary skill in the art upon consideration of the following detailed description of preferred embodiments and descriptions of the best mode of carrying out the invention.

DETAILED DESCRIPTION OF THE PREFERRED EMBODIMENTS

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

Figure 7:
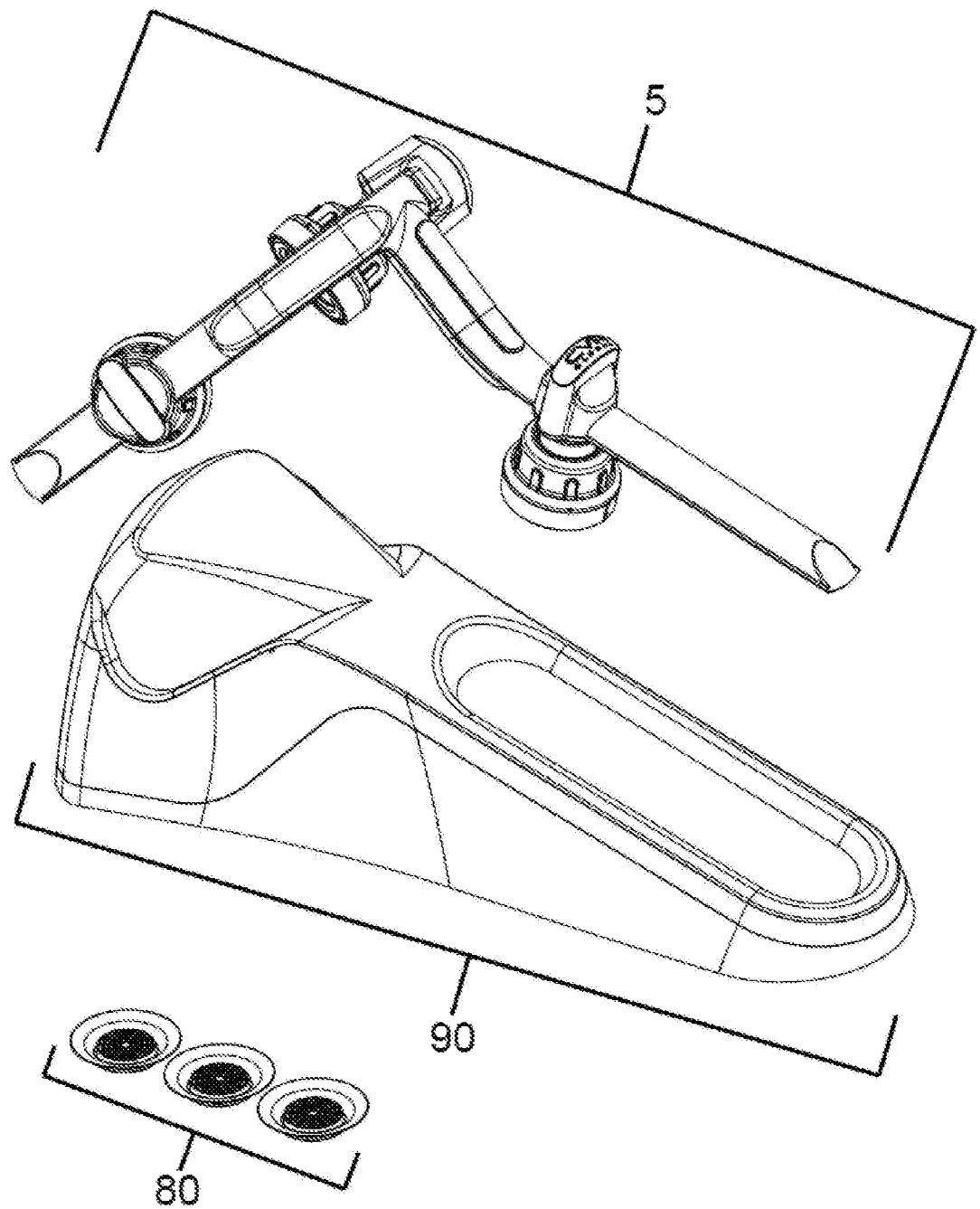
FIG. 7 is the sensor array and the base.

As used herein the term "yoke" or "array" are used interchangeably and refer to the structure having a stem and two arms, as depicted and described herein as element 5 as shown in FIG. 7. The array, as described in greater detail is suitable for positioning sensor pods onto a person for detecting and recording sounds generated by vortices in the carotid artery, as well as sounds from the heart.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

The present invention generally relates to an infrasonic sensor device, specifically to the yoke or array for holding a plurality of sensors in a set configuration. Attached to the yoke are sensor pads, for example, those described in U.S. Pat. No. 9,101,274, for example for non-invasive sensing and recording of blood flow and other related signals, specifically targeting vortices generated in the carotid artery. The sensed information can be used to detect the level of stenosis or occlusions, if any, of arteries and other related diagnosis of a living organism in the carotid artery.

The yoke 5 is particularly suited for use with a set of infrasonic, sensors configured as sensor pods 1 for measuring stenosis of the carotid artery in humans. In providing a sensing device for use with patients, a particular issue is the need to locate sensor elements near particular structures on the body. In an ideal world, every patient would be the same shape and size and modification of the structure would not be required. However, in practice, men, women, and children have significantly different shapes and sizes due to the amount of body mass, muscle, breast tissue, fat deposits, etc. Specifically, changes in body mass and shape between the neck and the torso create issues where the array must be modified to position one or more sensors in appropriate positions for acoustic sensing.

Therefore, as used on human patients, a difficulty in such devices is that people come in all shapes and sizes and that the array must be easily modified to fit these different shapes and sizes. One option would be to utilize different sized, fixed position sensing elements, due to the fragile nature of the sensing elements. However, constant movement and replacement of the sensing elements from one device to another would likely result in more damage to the sensing elements and increase the risk for the need for frequent replacement of these elements. Therefore, an array that provides the necessary stability and flexibility provides a great advantage in the array for use on patients.

A particular feature of the array is that it is adjustable and can be configured to account for the anatomical differences between individuals, while remaining sufficiently rigid to support the sensing elements. Furthermore, the shape and design of the array is particularly important to assist with orienting sensing elements to each portion of the array, such that sensing elements can easily be positioned adjacent to the neck for appropriate positioning to sense the carotid artery. At the same time, the materials and the angles utilized in the array provide appropriate resistance and a gentle force to compress the sensing element to the side of the neck for sensing. The shape and material thus provide an important feature to gently, but securely assist in positioning of the sensing elements and for testing patients for stenosis of the carotid artery.

The array is adjustably designed to fit a majority of adults and to be held by the patient or a third person when performing a carotid artery test. In a preferred embodiment, the array, when placed on the patient, imparts sufficient pressure on the patient so as to achieve a measurement of sufficient quality to accurately determine stenosis, while limiting the pressure applied to the carotid artery. The goal is to impart sufficient pressure to assist in positioning the sensing elements, and maintaining their position for about 2-3 minutes during a test, but gentle enough pressure as to not significantly impact or distort the shape and size of the carotid artery being assessed. Indeed, as a whole, the array and the sensing elements are designed to be a passive test that is non-emitting, non-invasive, and is configured so that anyone can conduct the test without requiring certification.

As shown in FIG. A, the array has a general "Y" shape composing a stem 10, and two arms 30 and 40. Each of the stem 10 and the left arm 40 and right arm 30 can support a sensor. The sensor pods 1, positioned on each of the arms 30, 40, are positioned proximate to the carotid arteries during a test, and a third sensor pod 1, positioned on the stem 10, is generally positioned near the sternum/heart.

Figure 1A:
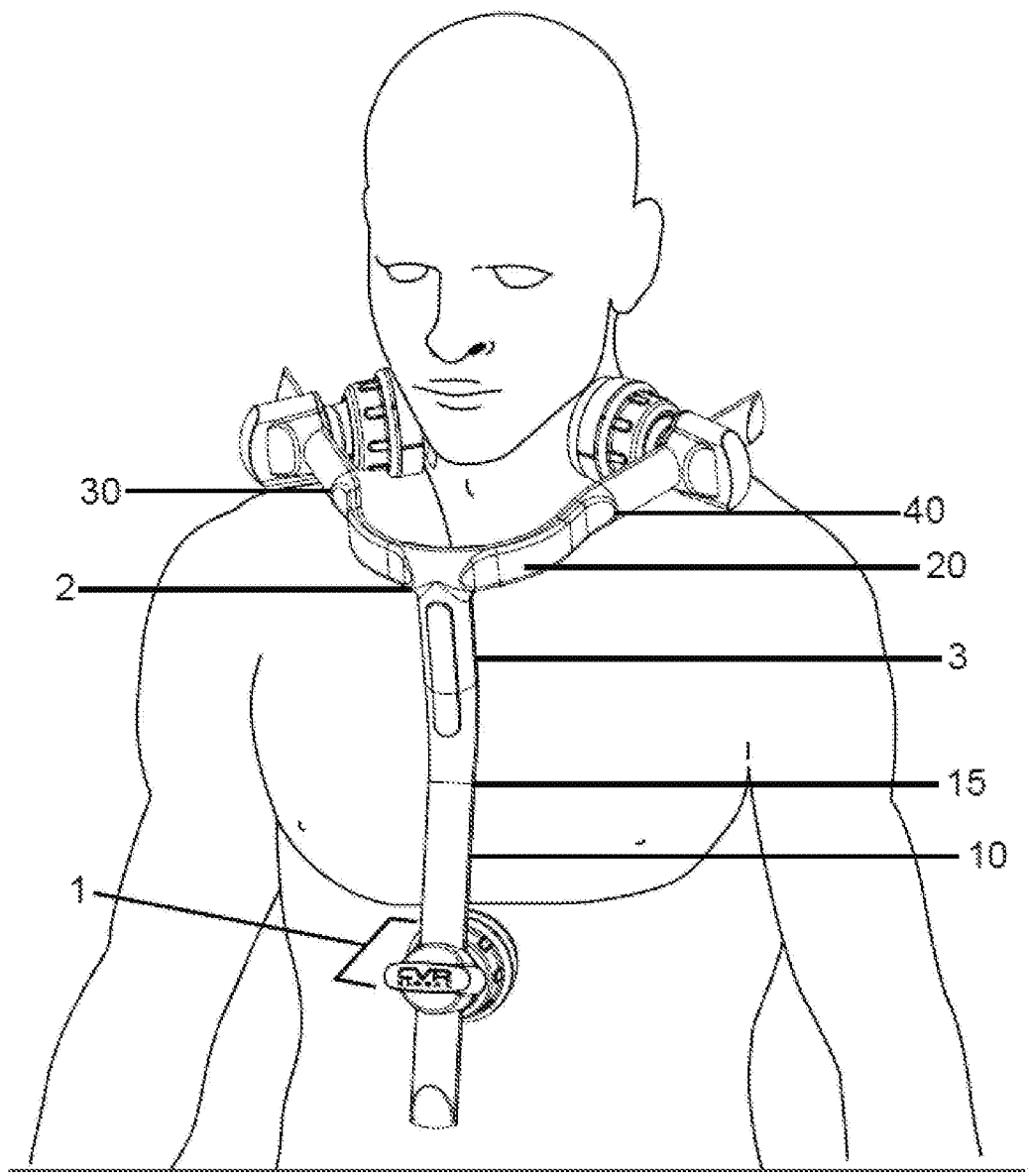
FIGS. 1A-1B are front perspective and side views of a sensor array.
Figure 1B:
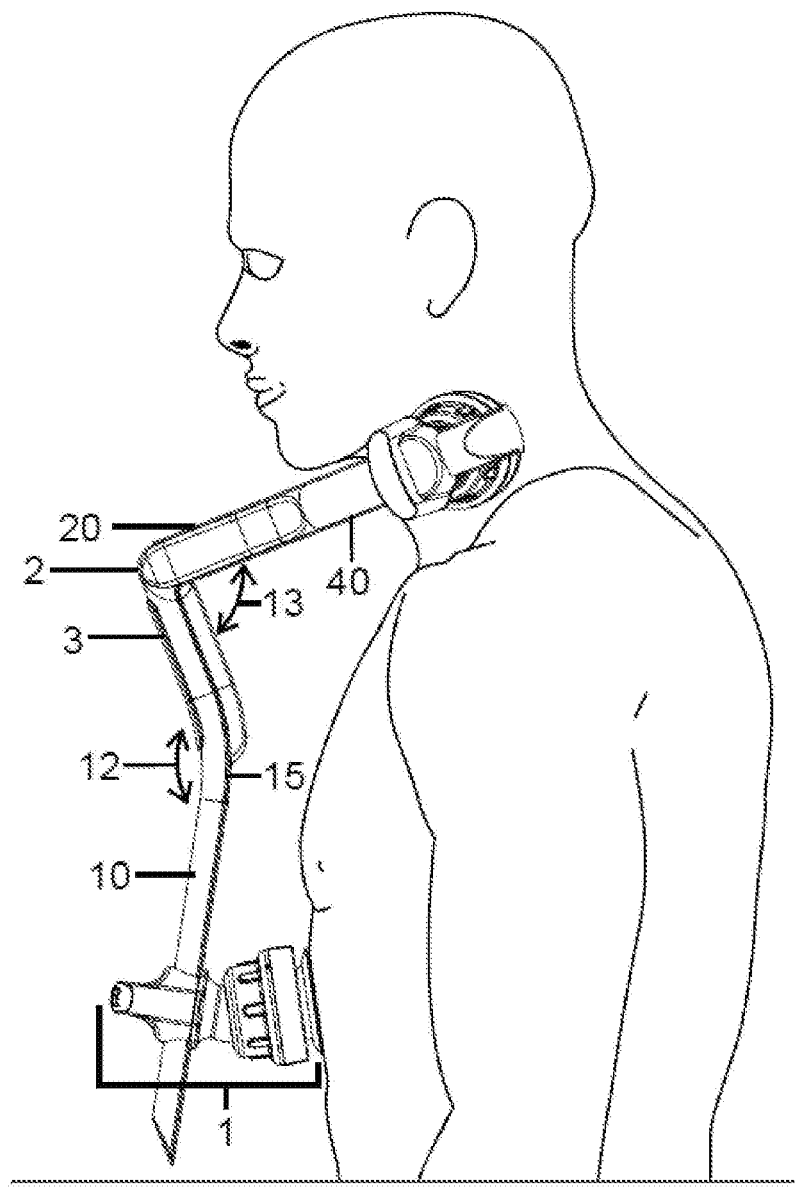

The upper two branches 30 and 40 or arms are flexibly connected to a shoulder 20 to allow for adjusting the sensors to properly position each sensing element on the carotid arteries regardless of the size and shape of the patient being tested. In this regard, as depicted in FIGS. 1A and 1B the upper two branches 30, 40 are biased inward toward each other as attached to the shoulders 20. The angle opening at the shoulder 20 is between about 90° and 145°. The angle can be easily modified, as each of the left and right arms 30, 40, and specifically the shoulder 20, are sufficiently flexible to be modified to fit a patient. The arms 30, 40 have a base, unflexed position, and can be bent/flexed outward or compressed inward, to fit patients needing a different orientation or width.

The shoulder 20 is attached to the neck vertex 2, which is thereafter connected to the neck 3, which is connected to a stem vertex 15, which is connected to the stem 10. The neck 3 and stem 10 connect at the stem vertex 15 at an angle of about 125° to about 175°. The positioning of the neck 3 and stem 10 allows for the bottom sensor pod 1 to be properly positioned over or near the heart.

Ultimately, the neck 3 connects to the neck vertex 2 which connects to the shoulder 20, which connects to the left and right arms 30 and 40. Each arm 30, 40 comprises a notched opening 31 and 41 as shown M FIG. 4, which aids in reducing weight and provides the appropriate modulus for bending the plastic material to fit different sized patients. Furthermore, the notched opening provides a track-like, feature to allow for the sensor pods 1 to slideably engage and move along the arms 30, 40 and the stem 10.

The plastic that is utilized is selected based at least in part on strength, stability, and ease of use. Therefore, preferred materials include polypropylene or other plastic materials. Such materials can be manufactured via any number of means, including printed, molded, extruded, or formed by one of ordinary skill in the art. The components can be manufactured separately and connected together or manufactured as a single piece having unibody construction. Alternatively, metal is used and selected based on the same criteria.

FIG. 1B further depicts the array 5 from a side profile, and clearly depicts angle 13 between the neck 3 and the shoulder 20. This angle 13 is important to assist in creating the necessary space between the patient and the device so as to ensure that the sensor pods 1 can be placed properly on the patient. Also shown is a stem vertex 15, which is a bent portion between the neck 3 and the stem 10. The stem vertex 15 has an angle 12 that assists in creating the necessary space between the patient and the device so as to ensure that the sensor pods 1 can be placed properly on the patient.

Figure 2:
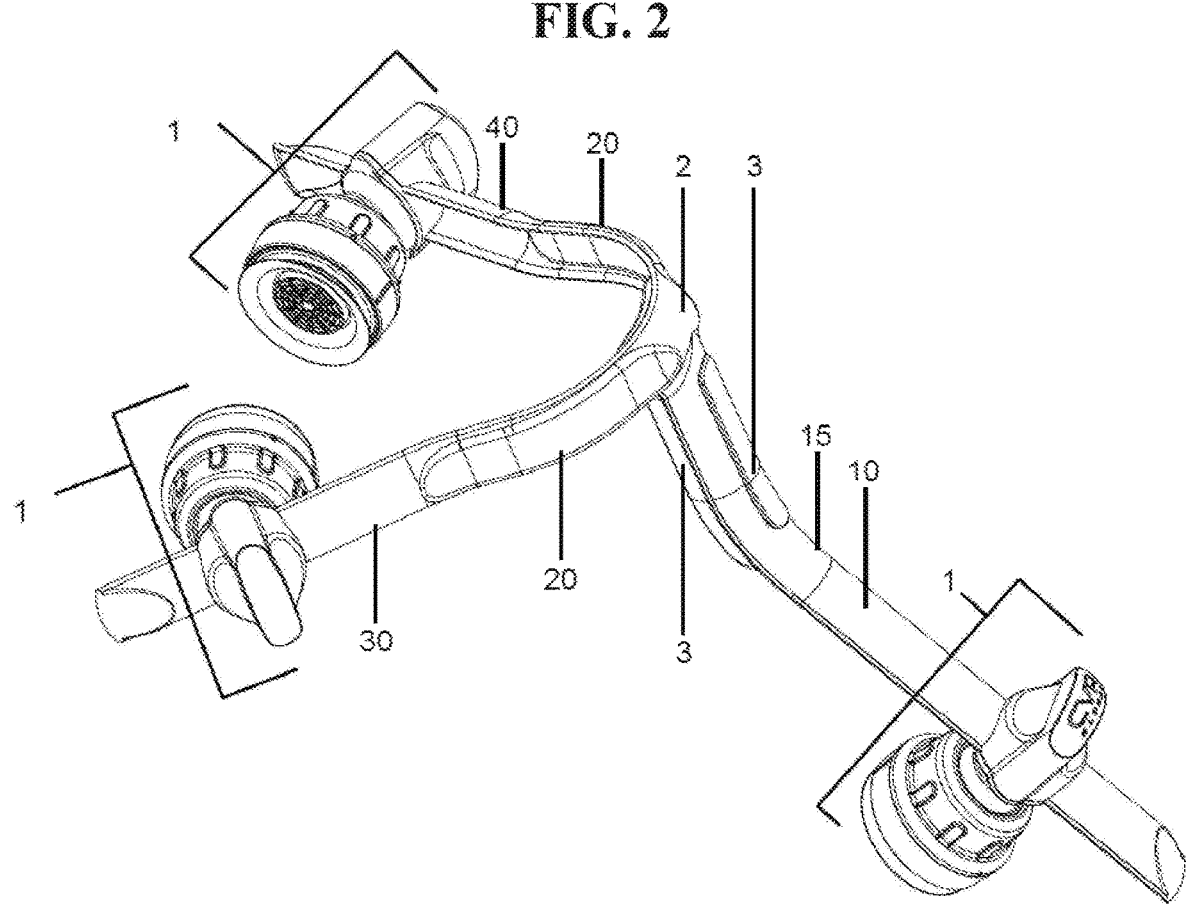
FIG. 2 is the sensor array.

FIG. 2 is a front perspective view and depicts specifically the orientation of the arms 30, 40 and, the angle there between. The neck vertex 2 is the center point connected to the shoulders 20, with each the left and right arms 30, 40 extending therefrom. In certain embodiments, the shape and orientation of the patient may result in the angle being uneven, or that greater flexion is required on one side of a patient than the other. Because of the design, such uneven flexion is easily accomplished and maintains each of the arms 30, 40 in proper position to take the test.

Figure 3:
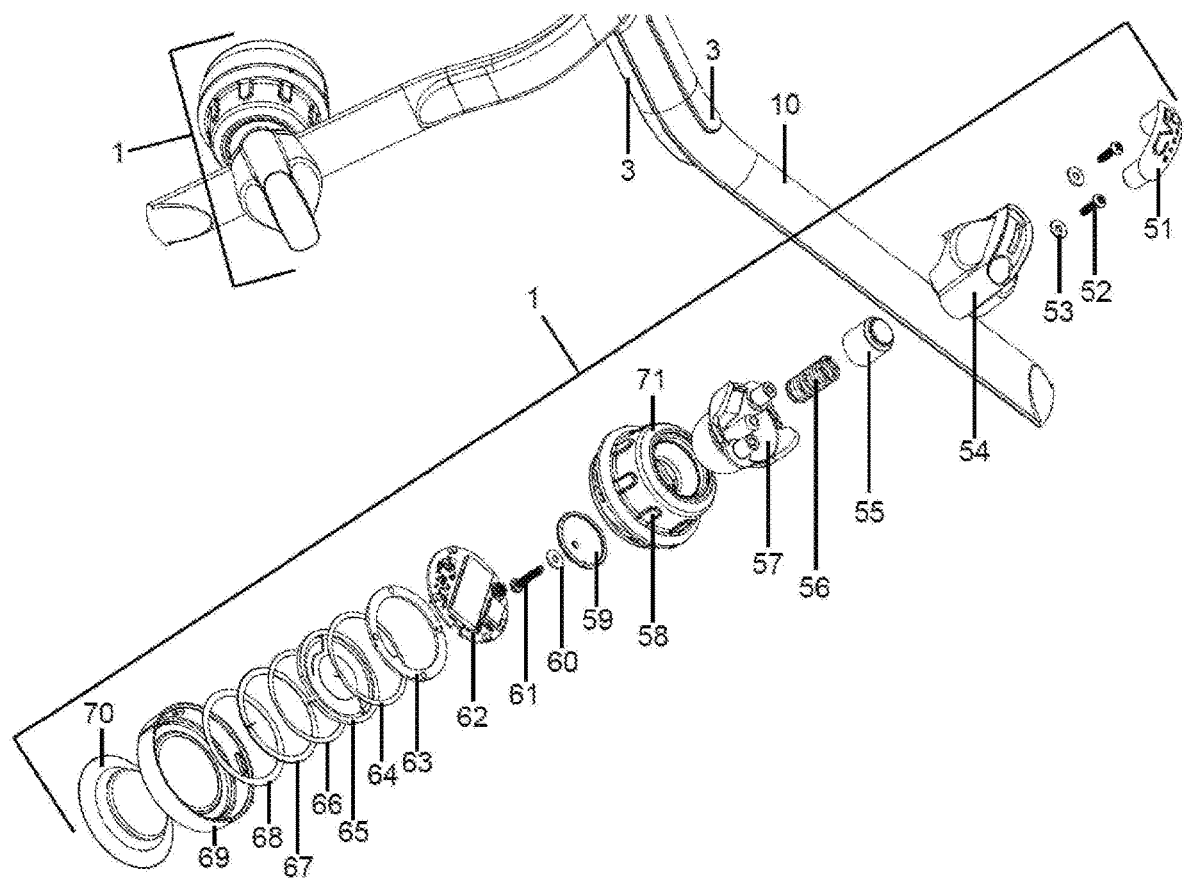
FIG. 3 is a sensor array showing a sensor pod in exploded view.

FIG. 3 is an exploded view of a sensor pod 1 showing the components that make up the sensor pod 1. A first sensor pod 1, configured to monitor the sternum/heart is slideably attached to the stem 10 at a lower end of the neck 3. Additional sensor pods 1 are attached to the arms 30, 40 and are configured to monitor the carotid arteries. The sensor pods are preferably all of a similar design.

Beginning at the portion of the sensor pod 1 that contacts the body, the sensor pod 1 comprises a diaphragm 70, configured as a sticky silicone gel pack, that extends out of disposable cap 69. The disposable cap 69 is configured to be removeably connected to housing 58, which is a clear elastomeric TPE over-mold. Arranged between the disposable cap 69 and the housing 58 are a printed circuit board (PCB) 62 having integrated circuits, a rechargeable battery, spring loaded contact, and led status lights arranged thereon, a contact PCB 63, pressure sensitive adhesive 64, a piezo element with a plastic ring 65, pressure sensitive adhesive 66, wireless charging coil 67, and pressure sensitive adhesive 68. The piezo element is configured to receive vibrations from the diaphragm 70 and output a signal to an input of the printed circuit board where the signal is processed by analog or digital signal processing circuits. The pressure sensitive adhesive 68 connects the wireless charging coil 67 to the disposable cap 69. It should be noted that other configurations are possible for the sensor pod 1. For example, the electronic components (PCB 62) can be arranged remotely. The silicone gel pack 70 is provided to contact the patient and transmit sounds to the piezo element. Other materials or configurations can be used in place of the silicone gel pack 70 including an epoxy/fiberglass diaphragm, a polyurethane-coated silicone, and the like.

In one embodiment, the PCB 62 is attached to the disposable cap 69 so that the sensing portion of the sensor pod 1 (elements 62-68) is replaceable. In one embodiment, the sticky silicone gel pack 70 is replaceable. In one embodiment, the PCB 62 is attached to the housing 58 so that the piezo element with a plastic ring 65, which may be attached to the disposable cap 69, is replaceable with the disposable cap 69.

The housing 58 is configured to be swivelably mounted to the array 5. The housing 58 has a socket 71 that mates with ball 57. In one embodiment, the housing 58 is attached to ball 57 by screw 61, washer 60, and compression friction washer 59. As shown in FIG. 3, the stem 10 serves as a guide or track for the sensor pod 1. A compression spring 56 biases friction plunger 55 against the stem 10. A cap 54 attaches to the ball 57 so that the stem 10 is between the cap 54 and ball 57. When attached, the friction plunger 55 presses against stem 10, within the track, to hold it in place. It should be noted that the pressure applied by the friction plunger 55 is sufficient to hold the senor pod 1 in a stationary location while still being slidingly adjustable. The cap 54 attaches to the ball 57 using screws 52 and washers 53. A decorative cap 51 is provided to plug the screw holes in the cap 54. It should be noted that rivets, glue, bayonet fingers, or the like can be used in place of screws or other threaded connections.

While FIG. 3 shows the sensor pod 1 attached to the stem 10, the sensor pod 1 may attach to the arms 30, 40 in a similar manner.

Figure 4:
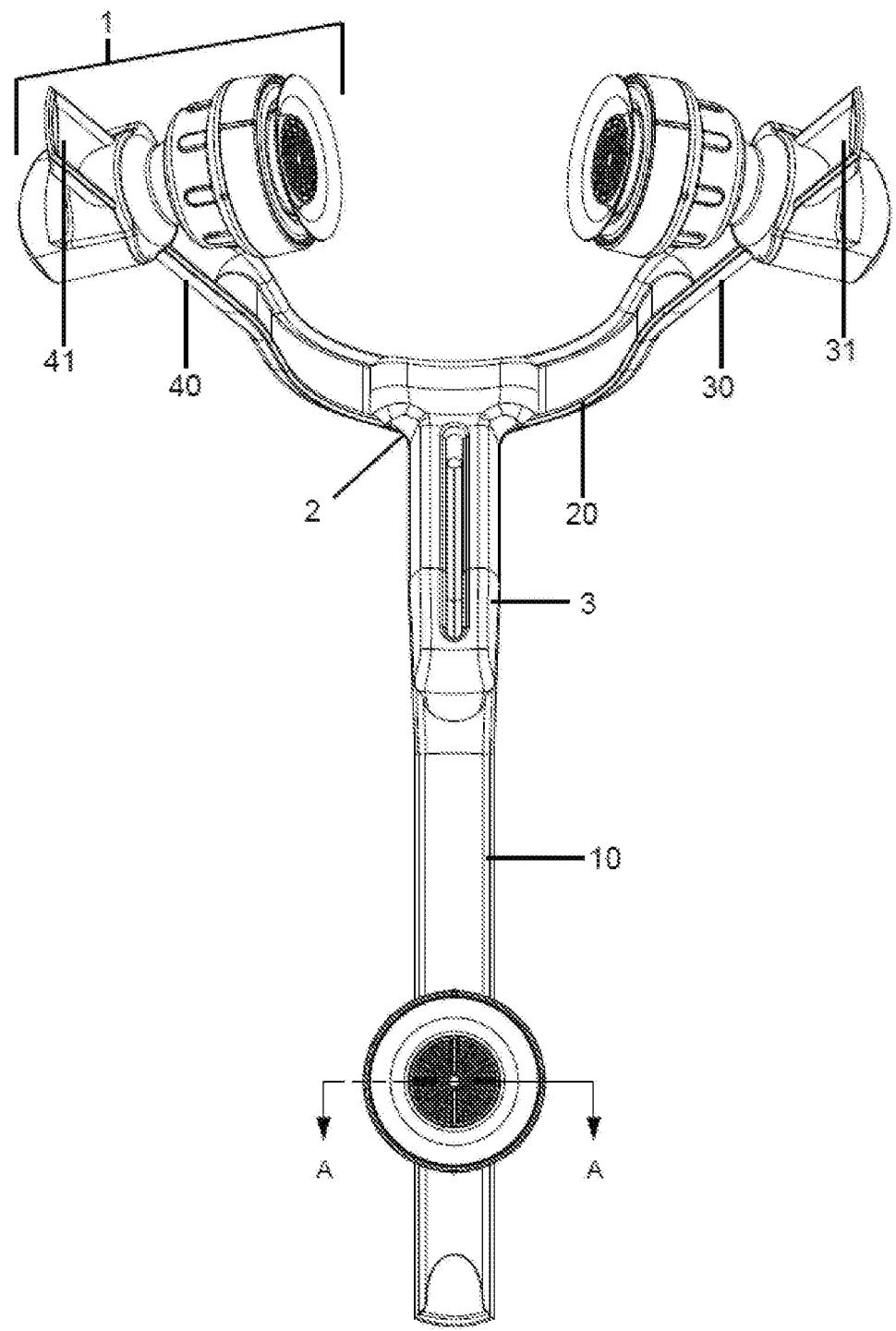
FIG. 4 is a further depiction of a sensor array.

FIG. 4 is another view of the array viewed from the perspective of the human body under test. Respective sensor pods 1 are moveably arranged on the stem 10 and arm 30, 40. Each arm 30, 40 comprises a notched opening 31 and 41 that serves as a track for the plunger 55. While not shown, the stem 10 can also be notched to make the stem 10 flexible and lightweight. The sensor pods are preferably configured so that the friction plunger 55 retains the sensor pod 1 in a given position.

Figure 5:
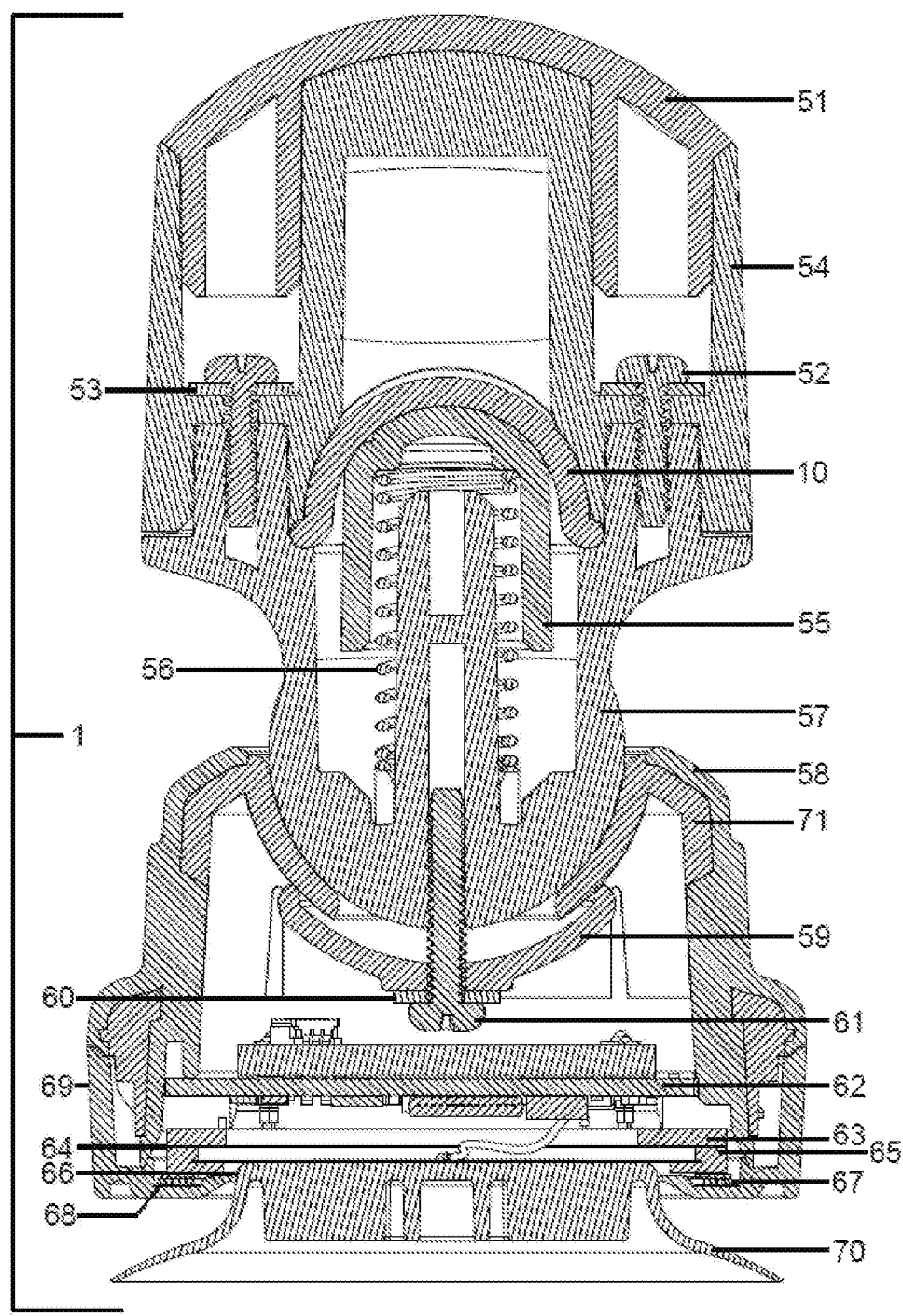
FIG. 5 is a cross sectional view of a sensor pod from FIG. 4.

FIG. 5 is a cross sectional view of a sensor pod 1 from FIG. 4. As shown, the housing 58 has a socket 71 that mates with ball 57. The ball 57 pivots in socket 71. The compression friction washer 59 acts as a stop to limit the pivot range of motion of the ball 57 and socket 71. In a preferred embodiment, the stem 10 is curved or notched. The friction plunger 55 is designed to have a complementary shape to insure sufficient contact. Alternatively, the stem 10 is planar and the friction plunger 55 has a substantially planar mating surface.

Figure 6:
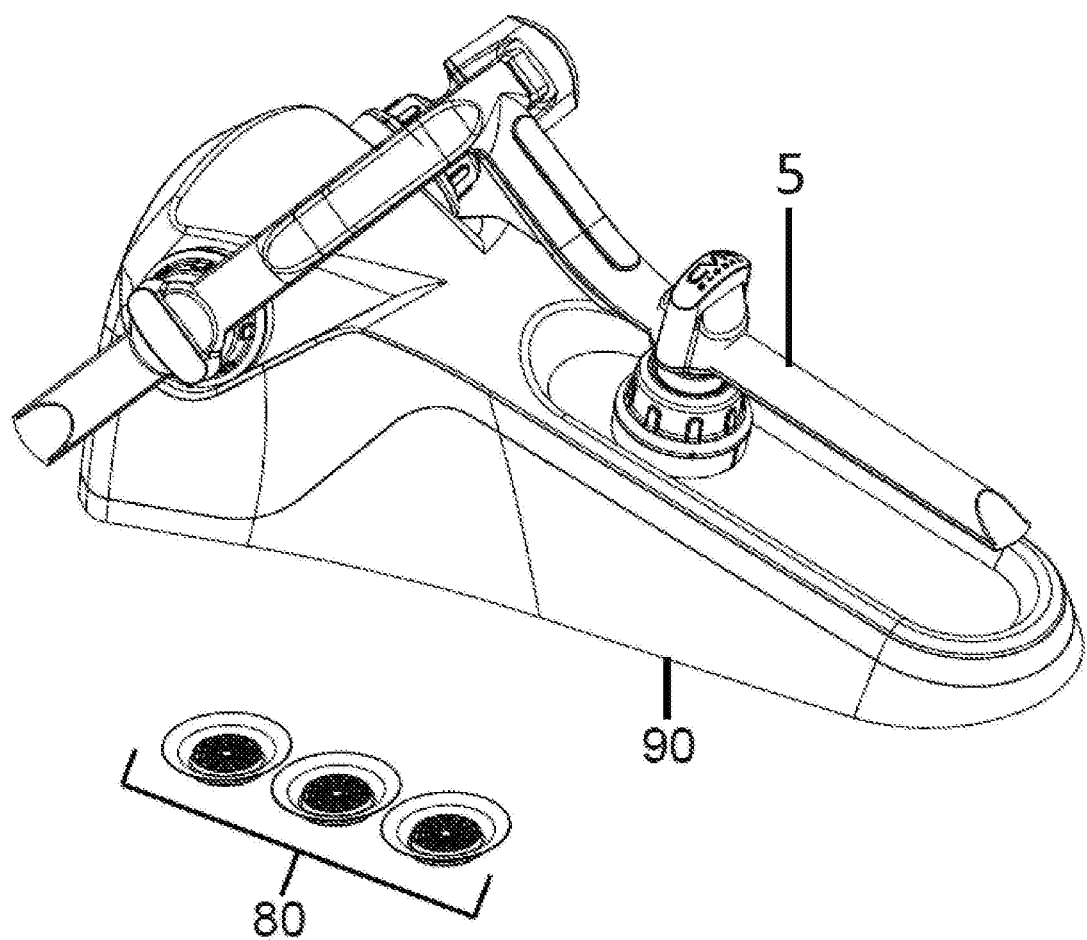
FIG. 6 is the sensor array in a base.

FIG. 6 depicts a sensor array 5 arranged onto a base 90, and replaceable sensor pads 80 adjacent to the base 90. The base 90 provides for several features for the array 5 including charging of the sensor pods 1, quality control of the sensor pods 1, and calibration of the sensor pods 1. In one embodiment, the base 90 and/or the sensor pods 1 have a charge indicator that indicates when charging, is occurring. Additionally, the charge indicator preferably indicates when charging is complete. FIG. 7 shows the array 5 removed from the base 90.

The base 90 charges the sensor pods 1 via inductive charging. Accordingly, each sensor pod 1 comprises a receptor, wireless charging coil 67, for receiving a charge front an induction charging device in the base 90. Alternatively, the array 5 can have a charging contact and the base 90 can have a corresponding charging contact to provide charging power to the sensor pods 1.

Figure 8:
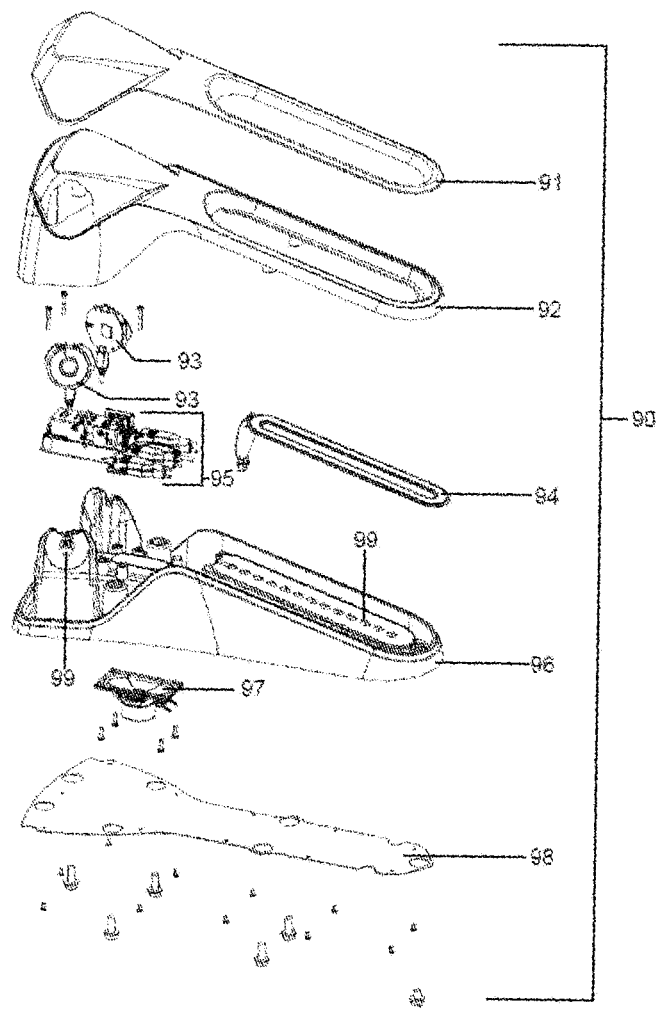
FIG. 8 is an exploded view of the components of the base.

FIG. 8 is an exploded view of the base 90 that provides charging and calibration for the array 5. The base 90 comprises a base enclosure top 92, a base enclosure bottom 96, and a bottom closure plate 98. A decorative elastomeric TPE over-mold 91 can be provided to protect the base 90 and the array 5. Arranged in the base 90 are an electronic module 95 and wireless charging coils 93, 94. The wireless charging coils 93, 94 are arranged to power the respective wireless charging coils 67 of the sensor pods 1. Also arranged in the base 90 is a calibration speaker 97. The electronic module 95 powers the wireless charging coils 93, 94. In one embodiment, the electronics module generates a calibration and verification signal to be reproduced by the calibration speaker 97. The base enclosure bottom 96 has one or more sound holes 99 arranged therein. Molded passages in the base enclosure bottom 96 allows for the sounds from the speaker 97 to pass through the holes 99 and resonate through the base enclosure top 91 and the over molder 91. This allows the piezo 65 to be tested and calibrated without any holes nit eh base enclosure top 92 or the over-mold 91.

In one embodiment, disposed within the base 90, and specifically adjacent to the cradle for each of the sensor pods 1, is a respective speaker 97. A computer is coupled to the base 90 for communication via a USB connection, Bluetooth, near field communication, RS-232, or the like. The computer couples to the speaker 97, and when sensor pods 1 are engaged to the base 90, a program is, executed by the computer system so that it performs a diagnostic and quality control test on each of the sensor pods 1.

The diagnostic and quality control procedure comprises a program that plays a known set of sounds generally corresponding to sounds that will be detected and recorded when measuring sounds on the body of a patient. These sounds include low and high frequency sounds, typically at low amplitudes corresponding to the sounds to be detected in the carotid arteries. Once the sound is played, the sensor pods 1 detect the sounds and convert the sound to a digital signal that is plotted and compared to a predetermined plot of the sounds that were played. Alternatively, an analog signal is plotted and compared with the predetermined plot. Each of the sensor pods 1 is independently tested to determine if it meets an acceptable standard. In one embodiment, and error message is generated if the sensor pod output is not within 10 percent of the predetermined plot at a given data point. Other standards can be used to determine an error condition exists. A range of 1 to 20 percent at each data point can be used to determine if the sensor pod 1 is not functioning, properly. Alternatively, the overall plot can be analyzed, instead of a point-by-point analysis, to determine if a sensor pod 1 is functioning properly. A calibration can be performed to shift the measured data, so that it corresponds with the predetermined plot.

If any of the sensor pods fails to detect an appropriate sound, then the system will notify the user of an error. In most instances, the error means that a particular sensor pod has exceeded its useful lifetime and is due for replacement. These devices theoretically have a lifespan of several hundred uses under ideal conditions. However, in a medical office, the continuous placing of the array 5 on or adjacent to a patient, and detecting and recording real sounds, may result in distortion after even a few uses. Accordingly, the system is able to determine whether the detected sounds are simply drift that is a slight change in the detected sounds, or whether there is an error or fault in one of the sensors. If there is only a slight drift, the system can calibrate each unit so that the measured noises from the system are consistent through use.

If the measured sounds are greater than a slight drift, the system notifies the user through images on a display, lights on the sensor pod, audible messages, or other manner to communicate the error, and identifies which sensor pod is faulty. A user can then quickly replace the faulty sensor pod and re-run the quality and calibration control program.

After the sensor pod is replaced and the quality control program is re-run, and the replacement sensor pod is confirmed to be working properly, the system will alert that it is ready for placing on a patient. Each of the sensor pods can be appropriately placed onto the patient.

Figure 9:
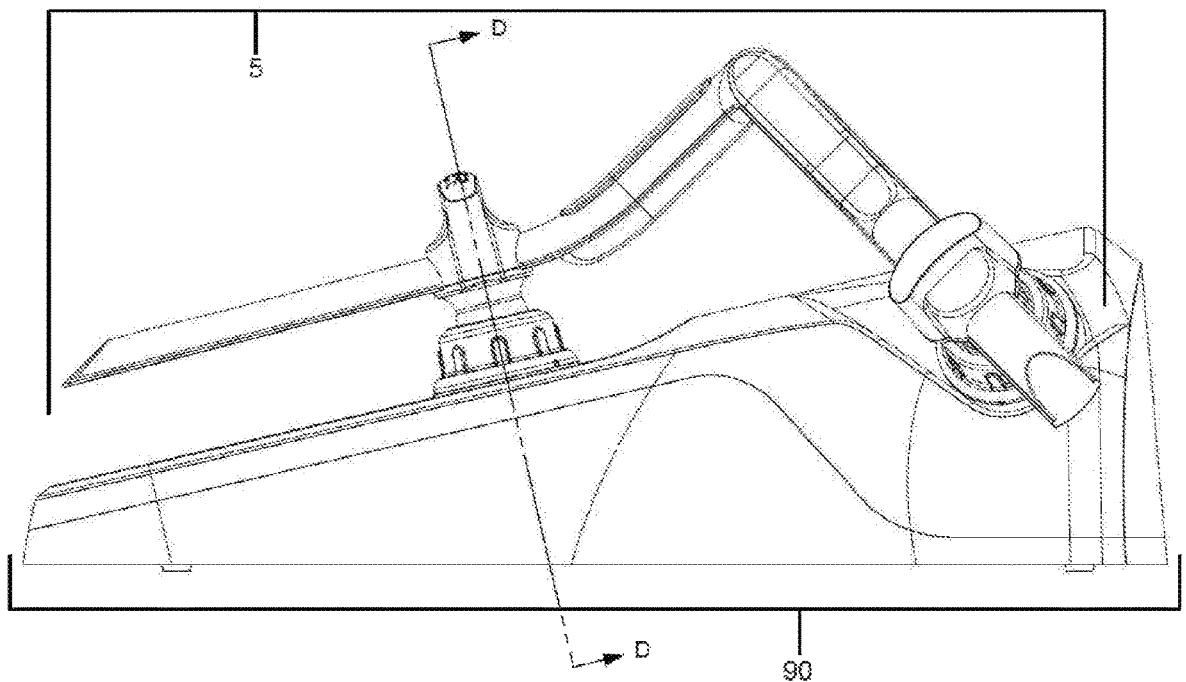
FIG. 9 is a side view of the sensor array in the base.

FIG. 9 is a side view of the sensor array in the base. As shown, the array 5 is supported by the sensor pods 1. The sensor pods 1 arranged on the arm 30, 40 are typically in a same position. Even when the pods 1 are moved along the arms 30, 40, they will generally rest in the appropriate holding portion of the base 90. However, depending on the patient, the sensor pod 1 on the stem 10 can be in one of a plurality of positions. The plurality of sound holes 99 accommodate the various positions of the sensor pod 1 on the stem 10.

Figure 10:
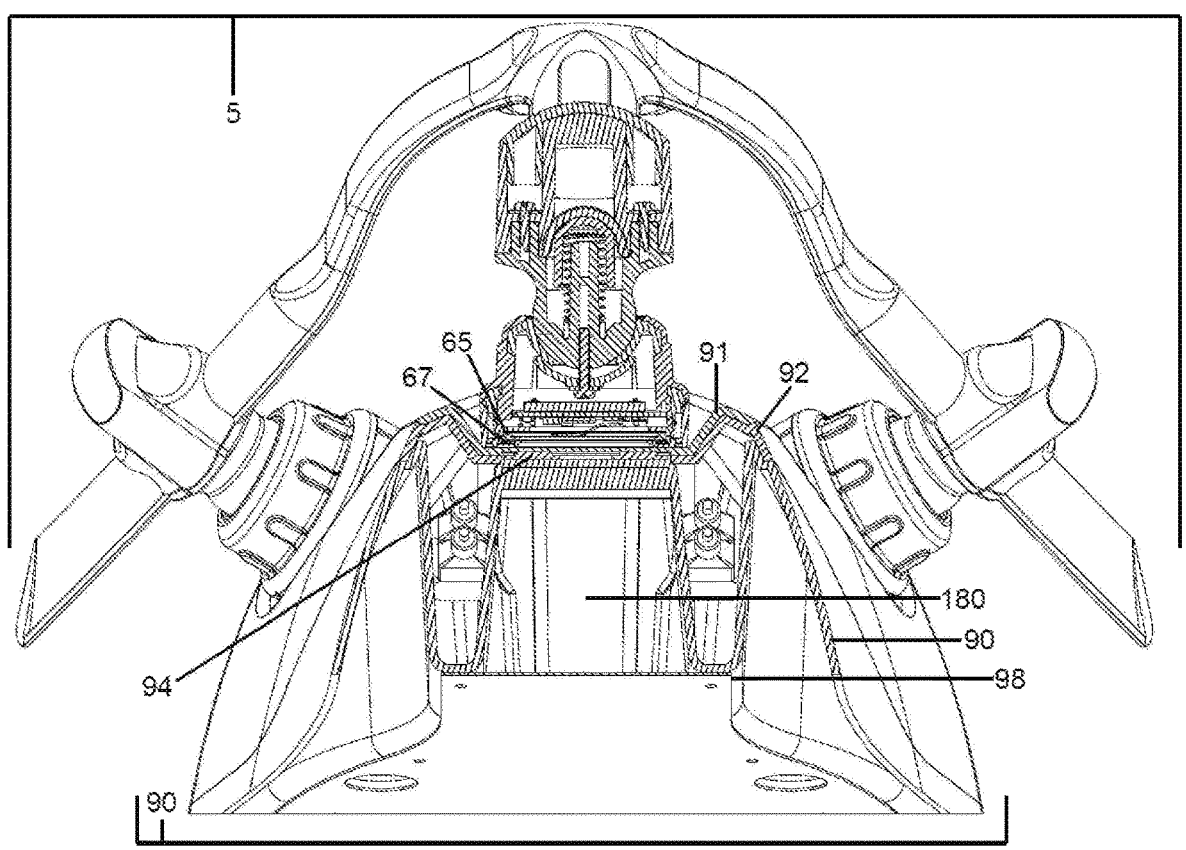
FIG. 10 is a cross sectional view of FIG. 9.

FIG. 10 is a cross sectional view of FIG. 9 at D-D. As shown, a sound chamber 180 is created by the base 90. The sound chamber 180 conveys the sounds from speaker 97 to the sensor pods 1. In one embodiment, the sound chamber 180 has a sensor that verifies the tones generated by the speaker 97 to insure that the base 90 is functioning properly.

Figure 11:
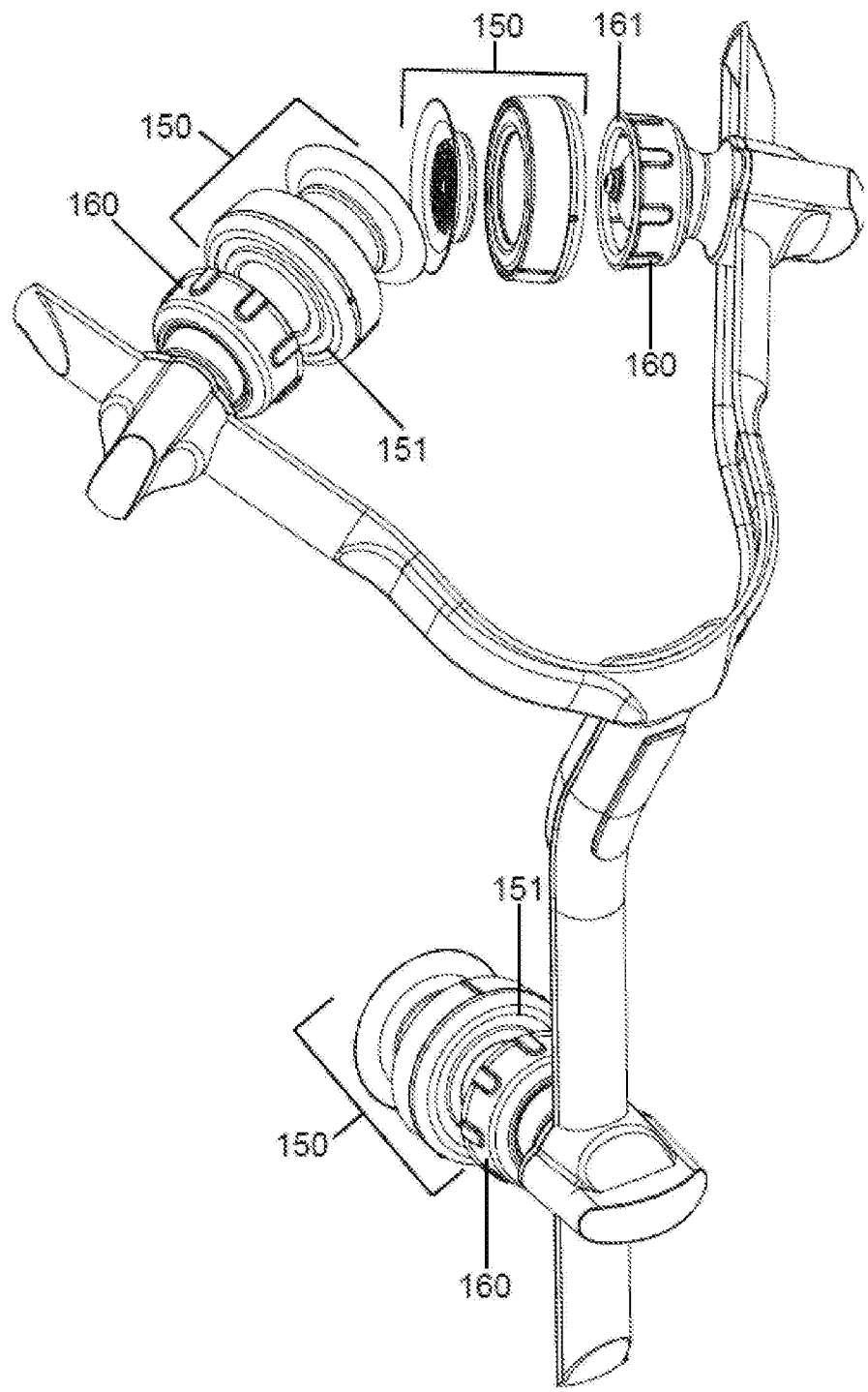
FIG. 11 is a sensor array and components of the sensor pods.

FIG. 11 is a sensor array 5 and sensor pods. As shown, the sensor pods comprise a pivoting attachment socket 160 attached to arms and stem of the array. The socket 160 includes attachment mechanism 161. The attachment mechanism 161 can be a molded thread, a magnet, hook and loop fastener, snap fit, bayonet mount, or the like. The remainder of the sensor pod 1 is a removable and disposable sensor portion 150, which includes a diaphragm. The disposable sensor portion 150 includes an attachment mechanism 151 that corresponds with attachment mechanism 161. When the sensor pod 1 has to be replaced, the sensor portion is removed from the socket 160 and replaced with a new disposable sensor portion 150. The new sensor portion is checked and calibrated as discussed above.

Figure 12:
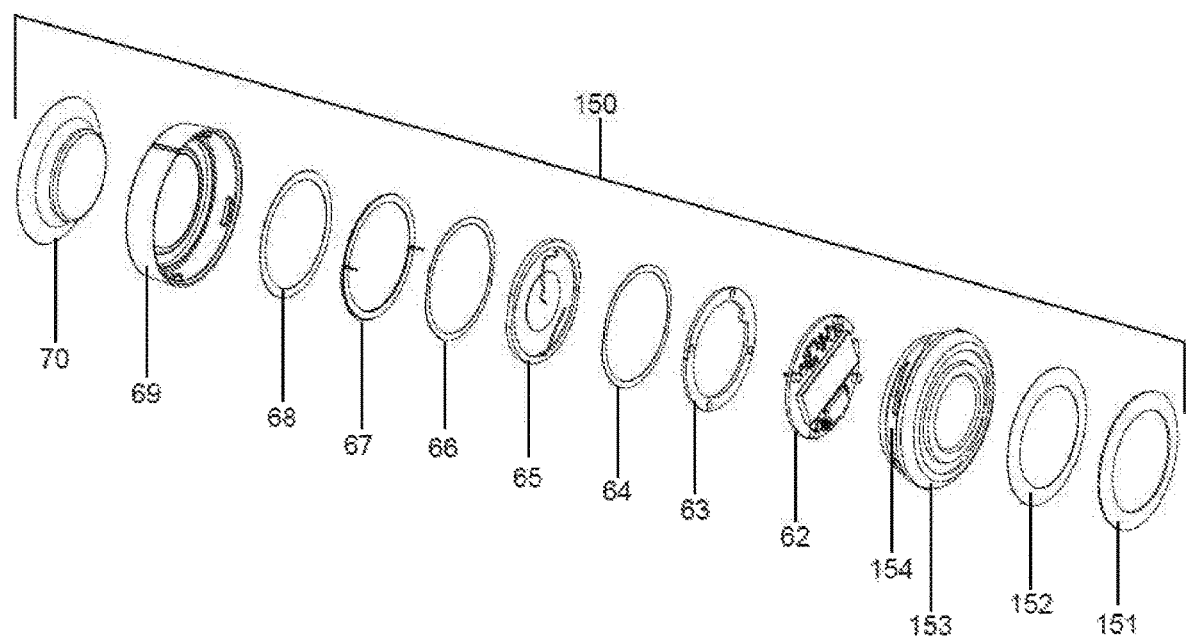
FIG. 12 is an exploded view of an embodiment of a disposable portion of a sensor pod.

FIG. 12 is an exploded view of an embodiment of a disposable sensor portion 150 portion of a sensor pod 1. The components are substantially the same as those discussed above with respect to FIG. 3 and will not be repeated here. The sensing components 62-68 are arranged between the disposable cap 69 and housing 153. The housing 153 has bayonet thread mount features that correspond with complementary elements on the disposable cap 69. Attachment mechanism 151 is affixed to housing 153 via a pressure sensitive adhesive 152. Alternatively, the attachment mechanism 151 is molded or co-molded with housing 153.

Having now fully described this invention, it will be understood to those of ordinary skill in the art that the methods of the present invention can be carried out with a wide and equivalent range of conditions, formulations, and other parameters without departing from the scope of the invention or any embodiments thereof.

What is claimed is:

1. An array for determining carotid artery stenosis in a human patient comprising:
    a neck having a longitudinal axis;
    coupled to the neck is a stem oriented in a first direction away from the longitudinal axis and defining an angle of between 125° and 175° as measured along the longitudinal axis;
    a neck vertex coupled to the neck with a pair of arms extending from the neck vertex in the opposite direction to the stem, wherein relative to one another the stem and the arms extend from the neck in opposing directions;
    the pair of arms defining an angle of between 225° and 270° as measured from the longitudinal axis of the neck to form a resting state, and wherein each of the stem and arms are made of a flexible material that is configured to be flexed away from the resting state of the flexible material;
    wherein the flexible material imparts a force to return back to the resting state; and wherein each of the arms and the stem are configured to receive a sensor pod within a track section and wherein each of the sensor pods comprises:
    a housing configured to be coupled to the arms and the stem;
    a disposable cap configured to removably attach to the housing;
    a diaphragm that extends out of the disposable cap;
    a printed circuit board having: integrated circuits, a rechargeable battery, a spring loaded contact, an input, and at least one LED status light;
    a piezo element configured to receive vibrations from the diaphragm and output a signal to the input of the printed circuit board; and
    a wireless charging coil configured to inductively charge the rechargeable battery.

2. The array for determining carotid artery stenosis in the human patient according to claim 1, wherein the stem and the neck are connected at a stem vertex.

3. The array for determining carotid artery stenosis in the human patient according to claim 2, wherein the stem and the pair of arms define the track section.

4. The array for determining carotid artery stenosis in the human patient according to claim 3, wherein the neck coupled to the stem defines an angle of about 165°, and wherein the angle between the neck and the arms is about 270°.

5. The array for determining carotid artery stenosis in the human patient according to claim 1, wherein the diaphragm is selected from the group consisting of a silicone gel pack, an epoxy/fiberglass diaphragm, and a polyurethane-coated silicone.

6. The array for determining carotid artery stenosis in the human patient according to claim 5, wherein the sensor pod is slideably attached to the track section of the stem and the arms.

7. An array for use in a carotid artery sensor configured as a Y-shaped structure comprising:
    a neck having a longitudinal axis;
    a stem coupled to the neck at a stem vertex, said stem oriented in a first direction away from the longitudinal axis at between 125° and 175°;
    a neck vertex coupled to the neck opposite the stem vertex;
    a left arm and a right arm coupled to the neck vertex, and said left arm and said right arm extending from the neck vertex in the opposite direction to the stem, wherein relative to one another, the stem and the arms extend from the neck in opposing directions along the longitudinal axis at an angle of about 225° and 270°;
    wherein the left arm and the right arm create a bell-like shape along a lateral axis from the neck; and wherein each of the arms and the stem define a track like structure and are configured to receive a sensor pod, and wherein the sensor pod comprises:

a housing configured to be coupled to the left arm, the right arm, and the stem;

a friction plunger defined to secure the sensor pod to the track like structure on the array;

a disposable cap configured to removably attach to the housing;

a diaphragm that extends out of the disposable cap;

a printed circuit board having: integrated circuits, a rechargeable battery, a spring loaded contact, an input, and at least one LED status light;

a piezo element configured to receive vibrations from the diaphragm and output a signal to the input of the printed circuit board; and a wireless charging coil configured to inductively charge the rechargeable battery.

8. The array for determining carotid artery stenosis according to claim 7 wherein said piezo element is positioned on said disposable cap.

9. The array according to claim 7, further comprising: a base configured to:

receive the Y-shaped structure;
inductively charge the Y-shaped structure;
calibrate the Y-shaped structure; and
test the Y-shaped structure.

* * * * *